United States Patent

Petitpierre

[11] 4,316,621
[45] Feb. 23, 1982

[54] PRESSURE-SENSITIVE OR HEAT-SENSITIVE RECORDING MATERIAL

[75] Inventor: Jean C. Petitpierre, Kaiseraugst, Switzerland

[73] Assignee: Ciba-Geigy Corporation, Ardsley, N.Y.

[21] Appl. No.: 192,382

[22] Filed: Sep. 30, 1980

[30] Foreign Application Priority Data

Oct. 26, 1979 [CH] Switzerland .................. 9629/79
Oct. 26, 1979 [CH] Switzerland .................. 9630/79

[51] Int. Cl.$^3$ .................. B41M 5/18; B41M 5/22
[52] U.S. Cl. .................. 282/27.5; 427/150; 427/151; 428/525; 428/913; 428/914; 428/320.6
[58] Field of Search .................. 282/27.5; 427/150, 151; 428/307, 525, 913, 914

[56] References Cited

U.S. PATENT DOCUMENTS 4,202,566 5/1980 Kosche .................. 282/27.5
4,212,345 7/1980 Kosche .................. 282/27.5

FOREIGN PATENT DOCUMENTS 2946830 5/1980 Fed. Rep. of Germany ..... 282/27.5

OTHER PUBLICATIONS

Chemical Reviews 75: 259–289 (1975), F. I. Luknitskii.
J. Chem. Soc. 4845 (1957), R. Hull.
J. f. prakt. Chemie 316: 304–314 (1974), B. Hesse, R. Moll.

Primary Examiner—Mary F. Downey
Attorney, Agent, or Firm—John P. Spitals; Edward McC. Roberts

[57] ABSTRACT

A pressure-sensitive or heat-sensitive recording material which comprises in its color reactant system, as developer for the color former, at least one compound of the formula

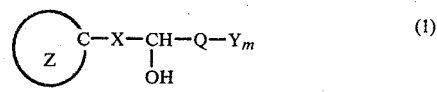

wherein the ring Z is a heterocyclic radical which does not contain a keto group adjacent to the linking carbon atom, X is the direct bond, —O—, —CHR—, —NR—, —CONR—, —SO$_2$NR—, —Nr$_1$—CO—NR$_2$—, —NR$_1$—CS—NR$_2$— or —NR$_1$—SO$_2$—NR$_2$—, wherein each of R, R$_1$ and R$_2$ independently is hydrogen, alkyl of at most 12 carbon atoms which is unsubstituted or substituted by halogen, cyano or lower alkoxy, or is benzyl, phenyl, or benzyl or phenyl each of which is substituted by halogen, methyl or methoxy, Q is carbon or an unsubstituted or substituted hydrocarbon radical, Y is halogen and m is 1 to 3. The grouping —O—Y$_m$ is preferably —C(Hal)$_3$, wherein Hal is halogen.

19 Claims, No Drawings

PRESSURE-SENSITIVE OR HEAT-SENSITIVE RECORDING MATERIAL

The present invention relates to a pressure-sensitive or heat-sensitive recording material which comprises in its colour reactant system, as developer for the colour former, at least one compound of the formula

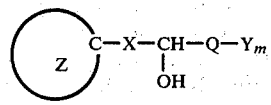 (1)

wherein the ring Z is a heterocyclic radical which does not contain a keto group adjacent to the linking carbon atom, X is the direct bond, —O—, —CHR—, —NR—, —CONR—, —SO₂NR—, —NR₁—CO—NR₂—, —NR₁—CS—NR₂— or —NR₁—SO₂—NR₂—, wherein each of R, R₁ and R₂ independently is hydrogen, alkyl of at most 12 carbon atoms which is unsubstituted or substituted by halogen, cyano or lower alkoxy, or is benzyl, phenyl, or benzyl or phenyl each of which is substituted by halogen, methyl or methoxy, Q is carbon or an unsubstituted or substituted hydrocarbon radical, Y is halogen and m is 1 to 3.

Preferred compounds of the formula (1) are those in which Q is carbon and m is 3.

Z is a heterocyclic ring system which is linked to X through a ring carbon atom and which does not contain a keto group (CO) adjacent to this linking carbon atom. The heterocyclic radical Z can be mononuclear or polynuclear and it contains 5 to 15, preferably 5 to 10, ring members, whilst 1 to 3, preferably 1 or 3, heteroatoms can be present as ring members.

Z is preferably a 5- or 6-membered heterocyclic ring system of aromatic character which does not contain a keto group adjacent to the linking carbon atom and which contains preferably oxygen, sulfur and/or nitrogen as ring members. Examples of such heterocyclic ring systems are: thienyl, furyl, pyrrolyl, pyrazolyl, imidazolyl, thiazolyl, pyridyl, pyrimidyl, thiadiazolyl, triazolyl or isothiazolyl radicals.

Z can also be a polynuclear, e.g. a bi- or trinuclear, heterocyclic ring system which preferably contains a fused benzene or naphthalene ring, e.g. a substituted or unsubstituted benzofurane, benzothiophene, indole, indazole, benzimidazole, benzothiazole, benzisothiazole, benzotriazole, naphthotriazole, quinoline or carbazolyl radical.

The mono- or polynuclear radicals Z can contain one or more identical or different substituents, e.g. halogen, cyano, nitro, hydroxyl, lower alkyl, lower alkoxy, lower alkylcarbonyl, lower alkoxycarbonyl, lower alkylamino, dilower alkylamino, N-lower alkylcarbamyl, N,N-di-lower alkylcarbamyl or phenyl.

The heterocyclic radicals Z can also be non-aromatic. Examples of such substituents are the partially or completely hydrogenated heterocyclic radicals, which can also be substituted, e.g. by lower alkyl, and which correspond to the above specified aromatic heterocyclic ring systems.

X is preferably the direct bond, —CHR— or —NR—. However, X can advantageously also be —O—, —CONR—, —SO₂NR—, —NR₁—CO—NR₂— or —NR₁—SO₂—NR₂—.

R, R₁ and R₂ are preferably hydrogen. Alkyl groups R, R₁ and R₂ may have 1 to 12 carbon atoms and can be straight chain or branched, for example methyl, ethyl, propyl, isopropyl, n-butyl, sec-butyl, n-hexyl, n-octyl or n-dodecyl. Substituted alkyl groups R, R₁ and R₂ are in particular cyanoalkyl, haloalkyl or alkoxyalkyl, each containing a total of 2 to 5 carbon atoms, e.g. β-cyanoethyl, β-chloroethyl, β-methoxyethyl or β-ethoxyethyl.

Preferred substituents in the benzyl and phenyl moiety of the radicals R, R₁ and R₂ are e.g. halogen, methyl or methoxy.

Q can be an aliphatic, cycloaliphatic, aliphatic-aromatic or aromatic hydrocarbon radical which is unsubstituted or substituted. An aliphatic radical Q is in particular a C₁-C₆alkylene radical, preferably a C₁-C₄alkylene radical, which can be straight chain or branched and substituted by halogen, carboxyl, —SO₃H, phenyl or halophenyl. A cycloaliphatic radical Q is in particular the cyclohexylene group. As an aromatic radical, Q is preferably diphenylene or, most preferably, phenylene which can be substituted by halogen, carboxyl, —SO₃H, lower alkyl or lower alkoxy.

Within the scope of the definition of the above radicals, lower alkyl and lower alkoxy usually denote those groups or group constituents which contain 1 to 5, especially 1 to 3, carbon atoms, e.g. methyl, ethyl, n-propyl, isopropyl, n-butyl, sec-butyl, tert-butyl or amyl, and methoxy, ethoxy or isopropoxy.

Throughout this specification, halogen as substituent of compounds of the formula (1) is e.g. fluorine, bromine or, preferably, chlorine.

In formula (1), X is preferably a —NH— group and, most preferably, the —NH—CO—NH— group.

Important colour formers of the formula (1) to be used in the practice of this invention have the formula

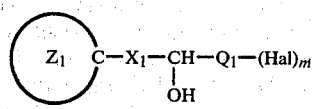 (2)

wherein the ring Z₁ is a mononuclear or binuclear heterocyclic radical which is unsubstituted or substituted by halogen, cyano, hydroxyl, lower alkyl, lower alkoxy, lower alkylcarbonyl, lower alkylamino, di-lower alkylamino, N-lower alkylcarbamyl, N,N-di-lower alkylcarbamyl or phenyl, and which does not contain a keto group adjacent to the linking carbon atom, X₁ is the direct bond, —O—, —CH₂—, CHR₃—, —NR₃—, —CONH—, —SO₂NH—, —NH—CO—NH— or —NH—SO₂NH—, wherein R₃ is lower alkyl, and Q₁ is carbon, C₁—C₅alkylene or phenylene, Hal is fluorine, chlorine or bromine, and m is 1 to 3.

The ring Z₁ preferably has aromatic character, R₃ is preferably methyl, and X₁ is in particular —O—, —CONH—, —SO₂NH—, —NH—CO—NH— or —NH—SO₂NH—.

Preferred compounds of the formula (2) are those of the formula

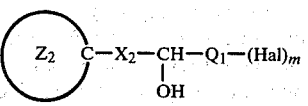 (3)

wherein the ring Z₂ is a mononuclear or binuclear heterocyclic radical which is unsubstituted or substituted by halogen, cyano, hydroxyl, lower alkyl, lower alkoxy, lower alkylcarbonyl, N-lower alkylcarbamyl, N,N-di-lower alkylcarbamyl or phenyl, and which does not contain a keto group adjacent to the linking carbon atom, and $X_2$ is the direct bond, $-CH_2-$, $-CHR_3-$ or $-NH-$, and $R_3$, $Q_1$, Hal and m have the given meanings.

Especially preferred compounds to be used as developers in the practice of this invention have the formula

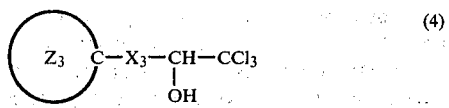

(4)

wherein the ring $Z_3$ is a furyl, thienyl, pyridyl, pyrimidyl, thiazolyl or quinolinyl radical, each of which is unsubstituted or substituted by halogen, cyano, hydroxyl, lower alkyl, lower alkoxy, N-lower alkylcarbamyl, N,N-di-lower alkylcarbamyl or phenyl, and $X_3$ is the direct bond, $-CH_2-$, $-O-$, $-NH-$, $-CONH-$ or $-NH-CO-NH-$. Preferably, $X_3$ is the direct bond, $-CH_2-$ or $-NH-$. The preferred meaning of $Z_3$ in formula (4) is pyridyl.

Very interesting developers, however, are compounds of the formula (4) in which $X_3$ is $-O-$, $-CONH-$ or $-NH-CO-NH-$ and $Z_3$ is a furyl, thienyl, pyridyl, pyrimidyl, thiazolyl or quinolinyl radical, each of which is unsubstituted or substituted by halogen, cyano, hydroxyl, lower alkyl, lower alkoxy or phenyl.

The most preferred compounds of the formula (4), however, are those in which $X_3$ is $-NH-CO-NH-$ and the ring $Z_3$ is furyl, pyridyl, pyrimidyl or quinolinyl.

Some of the compounds of the formulae (1), (2), (3) and (4) are known compounds, but constitute a novel class of developers or electron acceptors for colour formers. They can be obtained by methods which are known per se, for example by reacting 1 mole of a heterocyclic compound of the formula

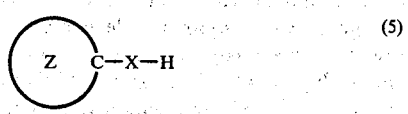

(5)

with an aldehyde of the formula $$Y_m-Q-CHO \qquad (6)$$

or the hydrate thereof, in which formulae Z, X, Y, Q and m have the given meanings.

The reaction is conveniently conducted in an inert solvent, optionally with the addition of a small amount of a basic catalyst. Examples of suitable solvents are cycloaliphatic or aromatic hydrocarbons, e.g. cyclohexane, benzene, toluene or xylene; chlorinated hydrocarbons such as chloroform, ethylene chloride or chlorobenzenes; ethers such as dioxane, diethyl ether, glycol dimethyl ether or tetrahydrofurane, as well as dimethyl formamide, dimethyl sulfoxide and acetonitrile. Examples of basic catalysts are: alkylamines, alkanolamines, piperidine, pyridine or ammonium acetate. The reaction can be carried out in the temperature range from 10° to 100° C., with the preferred range being from 20° to 80° C.

Known compounds of the formulae (1) to (4) and methods of obtaining them are described e.g. in Chemical Reviews 75 (1975), 259–289; R. Hull, J. Chem. Soc.

4845 (1957); and B. Hesse, A. Moll, J. f. prakt. Chemie, Vol. 316 (1974), 3041–314.

The starting materials of the formula (5) are heterocyclic compounds as defined herein which contain at least one reactive ring carbon atom or at least one reactive $R-CH_2-$ group, especially a methyl group or a reactive hydroxyl, amino, carbamyl, sulfamyl, ureido, thioureido or aminosulfamoyl group. These groups react with the aldehyde grouping of the compounds of the formula (6) to form the compounds of the formula (1).

Examples of heterocyclic starting compounds of the formula (5) are: furane, 2-methylfurane, N,N-diethyl-2-furamide, thiophene, collidine, 8-hydroxyquinoline, 8-aminoquinoline, 4-amino-2-methylquinoline, 2-phenyl-4-methyl-quinoline, 3-aminoindazole, 6-aminoindazole, 2-phenyl-4-methyl-6-methoxyquinoline, 3-aminopyridine, 2-amino-3-chloro-6-methylpyrimidine, quinaldine, 2-ethylquinoline, 5-aminotriazole, 5-aminopyrazole, 2-methylthiazole, 2-aminobenzoaminothiazole, 2-amino-6-methoxybenzothiazole and 2-amino-6-cyanobenzothiazole, as well as nicotinamide, isonicotinamide, 3-pyridylurea, 2-pyridylurea, 3-hydroxypyridine, 2-carbamyl-furane, 1-methyl-3-hydroxypiperidine, 5-sulfamylbenzoxazolone, 2-benzthiazolylsulfamide, 1,3-dimethyl-4-uracilylsulfamide, 2-hydroxy-9-methylcarbazole, 4-ureidophthalic anhydride.

Examples of starting aldehydes of the formula (6) are: chloroacetaldehyde, bromoacetaldehyde, fluoroacetaldehyde, trichloroacetaldehyde, tribromoacetaldehyde, trifluoroacetaldehyde, tribromopropionaldehyde, α-chlorocrotonaldehyde, trichlorobutyraldehyde, 2,3-dibromo-3,3-dichloropropional, 2,2,3-trichloropentanal, trichlorobenzaldehyde, 2,3-dichloro-3-phenylpropionaldehyde, 2,2,3-trichloro-3-phenylpropionaldehyde, 2-chloro-2,3-dibromo-3-phenylpropionaldehyde and 2,2,3-trichloro-3-(3'-chlorophenyl)-propionaldehyde.

In a further aspect, the invention relates to the novel compounds within the scope of the heterocyclic compounds of the formula (1) and having the formula

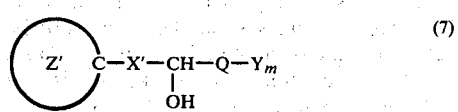

(7)

wherein the ring $Z'$ is a heterocyclic radical, $X'$ is $-O-$, $-CONR-$, $-SO_2NR-$, $-NR_1-CO-NR_2-$, $-NR_1-CS-NR_2-$ or $-NR_1-SO_2-NR_2-$, wherein each of R, $R_1$ and $R_2$ independently is hydrogen, alkyl of at most 12 carbon atoms which is unsubstituted or substituted by halogen, cyano or lower alkyl, or is benzyl or phenyl, or benzyl or phenyl which is substituted by halogen, methyl or methoxy, Q is carbon or an unsubstituted or substituted hydrocarbon radical, Y is halogen, and m is 1 to 3. Q is preferably carbon and the preferred value of m is 3. $X'$ is preferably $-O-$, $-CONR-$, $-SO_2NR-$, $-NR_1-CO-NR_2-$ or $-NR_1-SO_2-NR_2-$, and, most preferably, is the group $-NH-CO-NH-$.

These novel compounds of the formula (7) are especially advantageous developers for colour formers.

The definitions of the substituents Z, X, Q, Y and m in formula (1) also apply by analogy to the corresponding radicals $Z'$, $X'$, $Q'$, Y and m in formula (7).

Preferred novel compounds have the formula

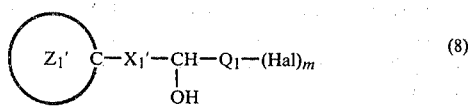

$$Z_1' \bigcirc C-X_1'-\underset{OH}{CH}-Q_1-(Hal)_m \qquad (8)$$

wherein the ring $Z_1'$ is a mononuclear or binuclear heterocyclic radical which is unsubstituted or substituted by halogen, cyano, hydroxyl, lower alkyl, lower alkoxy, lower alkylcarbonyl, lower alkylamino, di-lower alkylamino, N-lower alkylcarbamyl, N,N-di-lower alkylcarbamyl or phenyl, $X_1'$ is —O—, —CONH—, —SO$_2$NH—, —NH—CO—NH— or —NH—SO$_2$NH—, $Q_1$ is carbon, $C_1$-$C_5$alkylene or phenylene, Hal is fluorine, chlorine or bromine, and m is 1 to 3.

Particularly interesting compounds are those of the formula

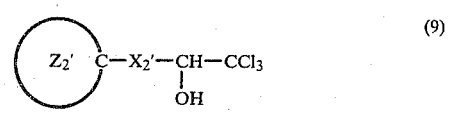

$$Z_2' \bigcirc C-X_2'-\underset{OH}{CH}-CCl_3 \qquad (9)$$

wherein the ring $Z_2'$ is a furyl, pyridyl, pyrimidyl, thiazolyl or quinolinyl radical which is unsubstituted or substituted by halogen, cyano, hydroxyl, lower alkyl, lower alkoxy or phenyl, and $X_2'$, is —O—, —CONH— or —NH—CO—NH—.

The most preferred colour developers within the group of compounds of the formula (9) above are those wherein the ring $Z_2'$ is furyl, pyridyl, pyrimidyl or quinolinyl, and $X_2'$ is —NH—CO—NH—.

The compounds of the formula (7) are obtained by reacting a heterocyclic compound of the formula

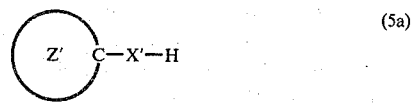

$$Z' \bigcirc C-X'-H \qquad (5a)$$

with an aldehyde of the formula $$Y_m-Q-CHO \qquad (6a)$$

or the hydrate thereof, in which formulae Z', X', Y, Q and m have the given meanings.

The novel compounds of the formulae (8) and (9) are obtained in the same manner.

The compounds of the formulae (1) to (4) and (7) to (9) are virtually colourless and odourless and are very reactive with the conventional colour formers, to that spontaneous, permanent and non-fading recordings or copies are obtained.

The colour formers suitable for the recording or copying material employed in this invention are known colourless or faintly coloured substances which, when brought into contact with the compounds of the formulae (1) to (4) and (7) to (9), become coloured or change colour. It is possible to use colour formers or mixtures thereof which belong e.g. to the classes of the phthalides, fluoranes, benzofluoranes, spiropyranes, azomethines, leuco-auramines, triarylmethane-leuco dyes, phenoxazines, phenothiazines, and of the chromeno or chromano colour formers. Examples of such suitable colour formers are: crystal violet lactone (Registered Trademark), 3,3-(bisaminophenyl)-phthalides, 3,3-(bis-substituted indolyl)-phthalides, 3-(aminophenyl)-3-indolyl-phthalides, 6-dialkylamino-2-n-octylaminofluoranes, 6-dialkylamino-2-arylaminofluoranes, 6-dialkylamino-3-methyl-2-arylaminofluoranes, 6-dialkylamino-2- or -3-lower alkylfluoranes, 6-dialkylamino-2-dibenzylaminofluoranes, bis-(aminophenyl)-furyl-, -phenyl-or -carbazolylmethanes, or benzoyl-leucomethylene blue.

The compounds of the formula (1) are suitable for use as colour developers in a pressure-sensitive, or especially heat-sensitive, recording material, which can also be a copying material.

A pressure-sensitive material consists for example of at least one pair of sheets, which contain at least one colour former dissolved in an organic solvent, and a developer of the formula (1). The colour former effects a coloured marking at those points where it comes into contact with the developer.

The developers of formula (1) can be used by themselves, in admixture with each other, or in admixture with known developers. These developers are preferably applied in the form of a layer to the face of the receiver sheet.

Typical examples of known developers are attapulgite clay, bentonite, acid-activated bentonite, halloysite, montmorillonite, silica, alumina, aluminium sulfate, aluminium phosphate, zinc chloride, kaolin or any clay or acidic organic compound, for example unsubstituted or ring-substituted phenols, salicylic acid or salicylates and their metal salts, or an acidic polymer, for example a phenolic polymer, an alkylphenolacetylene resin, a maleic acid/rosin resin, or a partially or completely hydrolysed polymer of maleic acid and styrene, ethylene or vinyl methyl ether, or carboxypolymethylene.

In order to prevent the colour formers contained in the pressure-sensitive recording material from becoming active prematurely, they are usually separated from the developer. This can advantageously be accomplished by incorporating the colour formers in foam-like, sponge-like or honeycomb-like structures. Preferably, the colour formers are enclosed in microcapsules, which usually can be ruptured by pressure.

When the capsules are ruptured by pressure, for example with a pencil, and the colour former solution is transferred in this manner to an adjacent sheet which is coated with the developer of the formula (1), a coloured area is produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as trichlorodiphenyl, and also tricresyl phosphate, di-n-butylphthalate, an aromatic ether such as benzylphenyl ether, a hydrocarbon oil such as paraffin or kerosene, an alkylated derivative of diphenyl, naphthalene or triphenyl, dibenzyl toluene, terphenyl, partially hydrogenated terphenyl, a benzylated xylene, or other chlorinated or hydrogenated, condensed aromatic hydrocarbons. Mixtures of different solvents are often used in order to obtain an optimum solubility for the colour formation, a rapid and intense colouration, and a viscosity which is advantageous for the microencapsulation.

The capsule walls can be formed evenly around the droplets of the colour former solution by coacervation; and the encapsulating material can consist of gelatin and gum arabic, as described e.g. in U.S. Pat. No. 2 800 457.

The capsules can also be formed preferably from an aminoplast or a modified aminoplast by polycondensation, as described in British Pat. No. 989 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers can be used for the production of a wide variety of known kinds of pressure-sensitive copying material. The various systems differ substantially from one another in the arrangement of the capsules, the colour reactants, i.e. the developers, and the support. A preferred arrangement is that in which the encapsulated colour former is in the form of a layer on the back of a transfer sheet and the developer is in the form of a layer on the face of a receiver sheet. However, the components can also be used in the paper pulp.

Another arrangement of the components is that wherein the microcapsules which contain the colour former, and the developer, are in or on the same sheet, in the form of one or more individual sheets, or are present in the paper pulp.

The capsules are preferably secured to the support by means of a suitable adhesive. As paper is the preferred support, these adhesives are principally paper-coating agents, for example gum arabic, polyvinyl alcohol, hydroxymethyl cellulose, casein, methyl cellulose, dextrin, starch or polymer lattices.

The paper employed comprises not only normal paper made from cellulose fibres, but also paper in which the cellulose fibres are replaced (partially or completely) by synthetic polymer fibres.

The compounds of the formula (1) are preferably employed as developers in a thermoreactive recording material. This recording material usually contains at least one carrier, one colour former, one solid developer and, optionally, also a binder. Thermoreactive recording systems comprise, for example, heat-sensitive recording and copying materials and papers. These systems are used e.g. for recording information, for example in electronic computers, teleprinters or telewriters, or in recording and measuring instruments. The image (mark) formation can also be effected manually with a heated pen. Laser beams can also be used to produce heat-induced marks. The thermoreactive recording material can be composed such that the colour former is dispersed or dissolved in one binder layer and the developer is dissolved or dispersed in the binder in a second layer. Another possibility consists in dispersing both the colour former and the developer in one layer. By means of heat the binder is softened at specific areas and the colour former comes into contact with the developer at those points where heat is applied and the desired colour develops at once. The developers of the formula (1) can be used by themselves, in admixture with each other, or in admixture with other known developers.

For this purpose it is known to employ the same developers as are used in pressure-sensitive papers, and also phenolic compounds, e.g. 4-tert-butylphenol, 4-phenylphenol, 4-hydroxydiphenyl ether, α-naphthol, β-naphthol, 4-hydroxymethylbenzoate, 4-hydroxyacetophenene, 2,2'-dihydroxydiphenyl, 4,4-isopropylidenediphenol, 4,4'-isopropylidene-bis-(2-methylphenol), 4,4'-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and organic, preferably aliphatic, dicarboxylic acids, for example tartaric acid, oxalic acid, maleic acid, citric acid, citraconic acid and succinic acid.

Fusible, film-forming binders are preferably used for the production of the thermoreactive recording material. These binders are normally water-soluble, whereas the colour formers and the developers are insoluble in water. The binder should be able to disperse and fix the colour former and the developer at room temperature.

The action of heat softens or melts the binder, so that the colour former comes in contact with the developer and a colour is able to form. Examples of binders which are soluble, or at least swellable, in water are e.g. hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. The preferred arrangement, however, is that in which the colour former and developer are contained in one layer in a water-soluble binder.

The thermoreactive coatings can contain further ingredients. To improve the degree of whiteness, to facilitate the printing of papers, and to prevent the heated pen from sticking, the coatings can contain e.g. talc, $TiO_2$, ZnO, $CaCO_3$, inert clays or also organic pigments, for example urea/formaldehyde polymers. In order to effect the colour formation only within a limited temperature range, it is possible to add substances such as urea, thiourea, acetamide, acetanilide, stearic amide, phthalic anhydride, phthalic nitrile or other appropriate fusible products which induce the simultaneous melting of the colour former and developer. Thermographic recording materials preferably contain waxes.

In the following Examples, which further illustrate the present invention, the percentages are by weight unless otherwise indicated.

EXAMPLE 1

A solution of 3 g of crystal violet lactone in 97 g of partially hydrogenated terphenyl is emulsified in a solution of 12 g of pigskin gelatin in 88 g of water of 50° C. A solution of 12 g of gum arabic in 88 g of water of 50° C. is then added, followed by the addition of 200 ml of water of 50° C. The resultant emulsion is poured into 600 g of icewater and cooled, whereupon coacervation is effected. A sheet of paper is coated with the suspension of microcapsules and dried. A second sheet of paper is coated with a compound of the formula

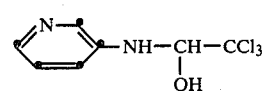

(11)

The first sheet and the sheet of paper coated with the compound of the formula (11) are laid on top of each other with the coated sides face to face. Pressure is exerted on the first sheet by writing by hand or typewriter and an intense blue copy develops on the sheet coated with the developer.

EXAMPLE 2

In a ball mill, 32 g of a compound of the formula

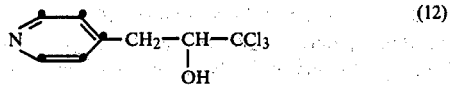

(12)

3.8 g of the distearylamide of ethylenediamine, 39 g of kaolin, 20 g of an 88% hydrolysed polyvinyl alcohol and 500 ml of water are ground to a particle size of about 5 μ. In a second ball mill, 6 g of 2-phenylamino-3-methyl-6-diethylamino-fluoran, 3 g of a 88% hydrolysed polyvinyl alcohol and 60 ml of water are ground to a particle size of about 3 μ.

Both dispersions are mixed and applied to paper to a dry coating weight of 5.5 g/m². An intense black colour of excellent lightfastness is produced by contacting the paper with a heated ball-point pen. The developers of the formula (13) listed in the following table can also be used in the same way as described in Examples 1 and 2.

$$Z_3-X_3-CH(OH)-CCl_3 \quad (13)$$

| Example | —X₃—Z₃ | m.p./°C. | n_D/°C. |
|---|---|---|---|
| 3 | (furan-2-yl) | | 1.5289/25 |
| 4 | (5-methyl-furan-2-yl) | | 1.5269/25 |
| 5 | (5-CON(C₂H₅)₂-furan-2-yl) | 95-96 | |
| 6 | (8-hydroxyquinolinyl) | 170-180 | |
| 7 | —NH—(4-Cl-6-CH₃-pyrimidin-2-yl) | 160-161 | |
| 8 | —CH₂—(4-C₂H₅-pyridin-2-yl) | 137 | |
| 9 | —CH₂—CH(O—C(CH₃)₂—O—CH₂—) | | 1.4852/26 |
| 10 | —CH₂—(4-C₆H₅-pyridin-2-yl) | 195 | |
| 11 | —CH₂—(2-C₆H₅-6-OCH₃-pyridin-?-yl) | 222 | |
| 12 | —CH₂—(thiazol-2-yl) | 124-126 | |
| 13 | —CH₂—(quinolinyl) | 148 | |
| 14 | —CH(CH₃)—(quinolinyl) | 117-118 | |
| 15 | —NH—CO—NH—(pyridin-3-yl) | 165-166 | |

The compound of Example 15 is obtained as follows: A mixture of 6.85 g of 3-pyridylurea [J. gen. Chem. USSR 20, 947 (1950)], 7 ml of chloral and 25 ml of ethylene chloride is stirred for 20 hours at 50°-55° C. and the precipitate that forms is collected by filtration. The product is purified by boiling it in acetone and then filtered once more, affording 8.5 g of a compound of the formula

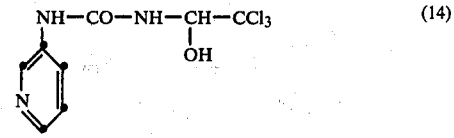

(14)

which melts at 165°-166° C. with decomposition.

What is claimed is:

1. A pressure-sensitive or heat-sensitive recording material which comprises in its colour reactant system, as developer for the colour former, at least one compound of the formula

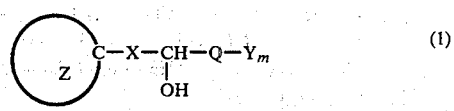

(1)

wherein the ring Z is a heterocyclic radical which does not contain a keto group adjacent to the linking carbon atom, X is the direct bond, —O—, —CHR—, —NR—, —CONR—, —SO₂NR—, —NR₁—CO—NR₂—, —NR₁—CS—NR₂— or —NR₁—SO₂—NR₂—, wherein each of R, R₁ and R₂ independently is hydrogen, alkyl of at most 12 carbon atoms which is unsubstituted or substituted by halogen, cyano or lower alkoxy, or is benzyl, phenyl, or benzyl or phenyl each of which is substituted by halogen, methyl or methoxy, Q is carbon or an unsubstituted or substituted hydrocarbon radical, Y is halogen and m is 1 to 3.

2. A recording material according to claim 1 which comprises a developer of the formula (1), wherein the heterocyclic ring Z is mononuclear or polynuclear, unsubstituted or substituted by halogen, cyano, nitro, hydroxyl, lower alkyl, lower alkoxy, lower alkylcarbonyl, lower alkoxycarbonyl, lower alkylamino, di-lower alkylamino, N-lower alkylcarbamyl, N,N-di-lower alkylcarbamyl or phenyl.

3. A recording material according to claim 1 which comprises a developer of the formula (1), wherein Q is carbon, $C_1$-$C_6$-alkylene, $C_1$-$C_6$-alkylene substituted by halogen, carboxyl, —$SO_3H$, phenyl or halophenyl; cyclohexylene, phenylene, diphenylene or phenylene substituted by halogen, carboxyl, —$SO_3H$, lower alkyl or lower alkoxy.

4. A recording material according to claim 1 which comprises a developer of the formula (1), wherein Q is carbon and m is 3.

5. A recording material according to claim 1 which comprises a developer of the formula (1), wherein X is the direct bond, —CHR— or —NR—, and R is as defined in claim 1.

6. A recording material according to claim 1 which comprises a developer of the formula (1), wherein X is —O—, —CONR—, —$SO_2NR$—, —$NR_1$—CO—$NR_2$— or —$NR_1$—$SO_2$—$NR_2$— and R, $R_1$ and $R_2$ are as defined in claim 1.

7. A recording material according to claim 6 which comprises a developer of the formula (1), wherein X is —NH—CO—NH—.

8. A recording material according to claim 1 which comprises a developer of the formula

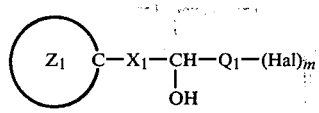

wherein the ring $Z_1$ is a mononuclear or binuclear heterocyclic radical which is unsubstituted or substituted by halogen, cyano, hydroxyl, lower alkyl, lower alkoxy, lower alkylcarbonyl, lower alkylamino, di-lower alkylamino, N-lower alkylcarbamyl, N,N-di-lower alkylcarbamyl or phenyl, and which does not contain a keto group adjacent to the linking carbon atom, $X_1$ is the direct bond, —O—, —$CH_2$—, —$CHR_3$—, —$NR_3$—, —CONH—, —$SO_2NH$—, —NH—CO—NH— or —NH—$SO_2NH$—, wherein $R_3$ is lower alkyl, and $Q_1$ is carbon, $C_1$-$C_5$-alkylene or phenylene, Hal is fluorine, chlorine or bromine, and m is 1 to 3.

9. A recording material according to claim 8 which comprises a developer of the formula (2), wherein $X_1$ is —O—, —CONH—, —$SO_2NH$—, —NH—CO—NH— or —$NHSO_2NH$—.

10. A recording material according to claim 8 which comprises a developer of the formula

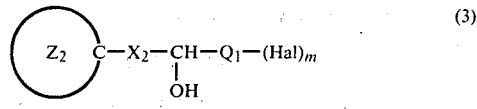

wherein the ring $Z_2$ is a mononuclear or binuclear heterocyclic radical which is unsubstituted or substituted by halogen, cyano, hydroxyl, lower alkyl, lower alkoxy, lower alkylcarbonyl, N-lower alkylcarbamyl, N,N-di-lower alkylcarbamyl or phenyl, and which does not contain a keto group adjacent to the linking carbon atom, and $X_2$ is the direct bond, —$CH_2$—, —$CHR_3$— or —NH—, and $R_3$, $Q_1$, Hal and m are as defined in claim 8.

11. A recording material according to claim 8 which comprises a developer of the formula

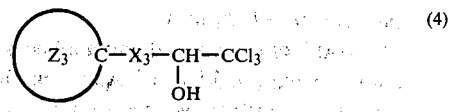

wherein the ring $Z_3$ is furyl, thienyl, pyridyl, pyrimidyl, thiazolyl or quinolinyl, each of which is unsubstituted or substituted by halogen, cyano, hydroxyl, lower alkyl, lower alkoxy, N-lower alkylcarbamyl, N,N-di-lower alkylcarbamyl or phenyl, and $X_3$ is the direct bond, —$CH_2$—, —O—, —NH—, —CONH— or —NH—CO—NH—.

12. A recording material according to claim 11 which comprises a developer of the formula (4), wherein $X_3$ is the direct bond, —$CH_2$— or —NH—.

13. A recording material according to claim 11 which comprises a developer of the formula (4), wherein $X_3$ is —O—, —CONH— or —NH—CO—NH— and $Z_3$ is furyl, thienyl, pyridyl, pyrimidyl, thiazolyl or quinolinyl, each of which is unsubstituted or substituted by halogen, cyano, hydroxyl, lower alkyl, lower alkoxy or phenyl.

14. A recording material according to claim 13 which comprises a developer of the formula (4), wherein $X_3$ is —NH—CO—NH— and the ring $Z_3$ is furyl, pyridyl, pyrimidyl or quinolinyl.

15. A pressure-sensitive recording material according to claim 1 which contains the colour former dissolved in an organic solvent.

16. A pressure-sensitive recording material according to claim 1, wherein the colour former is encapsulated in microcapsules.

17. A pressure-sensitive recording material according to claim 16, wherein the encapsulated colour former is applied in the form of a layer to the back of a transfer sheet and the developer of the formula (1) is applied in the form of a layer to the face of a receiver sheet.

18. A pressure-sensitive recording material according to claim 1, which contains the compound of the formula (1) together with one or more other colour developers.

19. A heat-sensitive recording material according to claim 1 which contains, in at least one layer, at least one colour former, at least one developer of the formula as indicated in claim 1 and at least one binder.

* * * * *